US010299818B2

(12) United States Patent
Riva

(10) Patent No.: US 10,299,818 B2
(45) Date of Patent: May 28, 2019

(54) DEVICE FOR TREATMENTS OF ENDOSCOPIC RESECTION/REMOVAL OF TISSUES

(75) Inventor: Raffaele Riva, Lugano (CH)

(73) Assignee: FRII SA, Luxembourg (LU)

( * ) Notice: Subject to any disclaimer, the term of this patent is extended or adjusted under 35 U.S.C. 154(b) by 0 days.

(21) Appl. No.: 13/378,546

(22) PCT Filed: Jun. 14, 2010

(86) PCT No.: PCT/IB2010/001411
§ 371 (c)(1),
(2), (4) Date: Jan. 25, 2012

(87) PCT Pub. No.: WO2010/146431
PCT Pub. Date: Dec. 23, 2010

(65) Prior Publication Data
US 2012/0123203 A1    May 17, 2012

(30) Foreign Application Priority Data

Jun. 16, 2009  (CH) ...................... 0940/09

(51) Int. Cl.
*A61B 1/12* (2006.01)
*B25F 5/00* (2006.01)
(Continued)

(52) U.S. Cl.
CPC ........ *A61B 17/32002* (2013.01); *A61B 1/018* (2013.01); *A61B 1/12* (2013.01);
(Continued)

(58) Field of Classification Search
CPC ...... A61B 17/320758; A61B 17/32002; A61B 17/320016; A61B 17/3207;
(Continued)

(56) References Cited

U.S. PATENT DOCUMENTS

| 5,562,609 | A | * | 10/1996 | Brumbach ....... A61B 17/32006 601/3 |
| 5,669,921 | A |   | 9/1997 | Berman et al. |
| 5,796,188 | A | * | 8/1998 | Bays ............................... 310/50 |
| 5,893,858 | A | * | 4/1999 | Spitz .............................. 606/170 |
| 6,203,518 | B1 | * | 3/2001 | Anis et al. ...................... 604/22 |
| 6,500,169 | B1 | * | 12/2002 | Deng ..................... A61B 17/00 200/302.2 |

(Continued)

FOREIGN PATENT DOCUMENTS

| DE | 31 36 880 | 4/1983 |
| WO | 96/29014 | 9/1996 |

OTHER PUBLICATIONS

International Search Report dated Nov. 4, 2010, corresponding to PCT/IB2010/001411.

*Primary Examiner* — Martin T Ton
(74) *Attorney, Agent, or Firm* — Silvia Salvadori

(57) ABSTRACT

A device (1) for treatments of endoscopic resection/removal of tissues, includes: a handpiece apt to be held by an user; an external tubular element (3) having a proximal end, a distal end and a cutting aperture disposed at the distal end; an internal tubular element (4) apt to be pivotally housed in the external tubular element (3) and having a proximal end, a distal end and a cutting tip at its distal end. The device also includes guide elements (5) for rotating and/or oscillating the internal tubular element (4) with respect to the external tubular element (3). The guide elements (5) include an electric motor (19) and electric feeding element for the electric motor (19) and are contained completely inside the handpiece (2).

11 Claims, 6 Drawing Sheets

(51) Int. Cl.
   *A61B 17/00* (2006.01)
   *A61B 17/32* (2006.01)
   *A61B 1/018* (2006.01)
   *A61B 17/22* (2006.01)

(52) U.S. Cl.
   CPC ...... *B25F 5/008* (2013.01); *A61B 2017/0023* (2013.01); *A61B 2017/00398* (2013.01); *A61B 2017/00734* (2013.01); *A61B 2017/22079* (2013.01)

(58) Field of Classification Search
   CPC .... A61B 17/3205; A61B 2017/320028; A61B 2017/320032; A61B 2017/320024
   USPC .................................................. 606/167, 180
   See application file for complete search history.

(56) References Cited

U.S. PATENT DOCUMENTS

| | | | |
|---|---|---|---|
| 6,689,146 B1* | 2/2004 | Himes | 606/167 |
| 6,846,314 B2* | 1/2005 | Shapira | A61B 10/025 604/35 |
| 7,077,845 B2* | 7/2006 | Hacker | A61B 17/32002 606/180 |
| 2002/0040229 A1* | 4/2002 | Norman | A61B 17/32002 606/180 |
| 2004/0092992 A1* | 5/2004 | Adams et al. | 606/180 |
| 2005/0159752 A1* | 7/2005 | Walker et al. | 606/80 |
| 2006/0206134 A1* | 9/2006 | Conquergood | A61B 17/32001 606/180 |
| 2007/0010823 A1 | 1/2007 | Kucklick | |
| 2008/0234715 A1 | 9/2008 | Pesce et al. | |

* cited by examiner

DEVICE FOR TREATMENTS OF ENDOSCOPIC RESECTION/REMOVAL OF TISSUES

RELATED APPLICATIONS

This application is a US national phase application of international application number PCT/IB2010/001411, filed 14 Jun. 2010, which designates the US and claims priority to Swiss (CH) application 00940/09 filed 16 Jun. 2009, the contents of each of which are hereby incorporated by reference as if set forth in their entireties.

FIELD OF THE INVENTION

The present invention relates to a device for treatments of endoscopic resection/removal of tissues. In particular, the invention relates to an endoscopic device for resection treatments of soft tissue or osseous tissue (with relative removal of the fragments produced by such an action).

BACKGROUND OF THE INVENTION

As an alternative to the traditional surgery, which requires a relatively wide incision to access to the surgical site inside the human body, the endoscopic procedures utilize natural accesses or as an alternative the creation of small portals (minimal tissular incisions); therefore often reference is made to the endoscopic surgery with the term of mini-invasive surgery. The two main advantages of the endoscopic surgery are the more rapid healing of the tissues after the surgical operation and the lesser exposition of internal tissues to the risk of an infection. The technological developments in this surgical field, also defined "closed", have led to the realization of many minimally invasive instruments, as the access to the surgical site is made through one or more portals. Such instruments must be sufficiently elongated and smooth to permit the entrance and the use with a minimum trauma for the surrounding tissues. A portion of the instrument, usually indicated as "distal portion", is so conceived in order to have access to the surgical site; the opposite portion, usually indicated as "proximal portion", remains at the outside of the body of the patient. The distal portion of the instrument is typically provided for treating the tissue with which it comes in contact, its shape and dimensions being therefore properly studied in function of the particular surgical operation to which it is destined.

The proximal portion is instead provided with a mechanism to control from the outside of the body of the patient the above function. The motorized endoscopic surgical instruments, used in the "closed" surgery, often identified as endoscopic "shavers", are typically made by a pair of coaxial tubular concentrically disposed elements: an external element ending distally with an aperture or "cutting window" and a rotary internal element having a sharp surface at the cutting window. The rotary action of the internal tubular element produces by abrasion the removal or the finishing of the tissue, this process being defined as "resection".

As in each surgical action, also in the endoscopic surgery the presence of two well distinct fields is provided: the sterile field, the one in close contact with the patient, whereby the surgeon will perform his operation, and the one definitely separated from the patient and from any object coming in contact with it. Only suitably treated personnel and instruments can access to the sterile field (sterilization processes for the instruments, washing pre-operatory processes and adoption of protective aids for the personnel, as gloves and coats); all that can not enter in contact with the sterile field must rigorously remain outside it.

US2007/0010823 describes a "shaver" for arthroscopic operations and a system for performing the suction and the irrigation during a medical procedure with the above "shaver".

U.S. Pat. No. 5,669,921 describes a cutting device comprising:

an elongated external having a proximal end, a distal end and at said proximal end a bushing to permit the attachment of the external tube to an electrically fed sleeve; and an elongated internal tube apt to be received in said external tube, having a proximal end, a distal end, an internal aperture at said distal end, a cutting tip and a bushing disposed at the proximal end, the bushing permitting the connection of the internal tube to guide means for the cutting device.

The Applicant has noted that in the endoscopic "shavers" actually existing and/or in those described above the internal tubular element is brought in rotation and controlled by a handpiece having internally a small electric motor: the actuation and control are made either by pushbuttons positioned on the sleeve itself or by pushbuttons positioned on a pedal board. In both cases the power and the control signals arrive at the sleeve through a wire connected with an external bracket. This "bracket" is usually disposed on a trolley sufficiently distant from the operation field in order not to contaminate the sterile field. The handpiece (which comes in contact with the sterile field) undergoes a sterilization treatment before each surgical operation; the bracket having to remain out of each contact with the sterile zone, is housed out of the aforesaid field; in the actually existing systems, a connection wire is provided between handpiece and "bracket". Such connection wire before each use is treated in order to render it completely sterile and at the preparation of the surgical operation it is assembled from one side with the (sterile) handpiece and from the other side with the (non sterile) bracket. In the actually existing "shavers" the handpiece is made of a metallic material, so it has a not negligeable weight, and the connection wire has a weight and encumbrance such to limit the handling of the operator.

The personnel of the operation room which is responsible for the treatment and the management of the instrument at the end of each operation has to perform the washing (with suitable disinfectants and detergents) and then the sterilizing of the resterilizable parts (handpiece and wire); the cleaning and the sterilization negatively affect the useful life of the sterilizable components.

The personnel of the operation room must further perform the storing in suitable containers which guarantee the sterility, with a consequent waste of time and space consumption.

Nevertheless the personnel of the operation room must perform the maintenance of the non sterilizable components, i.e. the bracket and the pedal board if present, by making periodical inspections which can require more complex technical interventions by qualified personnel.

The Applicant has also noted that in the present technological solutions in the market or for example described in the aforesaid documents, some non satisfied needs remain and some limits not yet overcome; man maneuverability, ergonomics, safety referring to sterility, simplification of management and maintenance.

SUMMARY OF THE INVENTION

The Applicant has found that with a device for endoscopic resection/removal of the tissues having an electric motor and electric feeding means contained inside the handpiece, it is possible to increase the maneuverability and the ergonomics of the device itself by simplifying at the same time the management and the maintenance.

In one of its first aspects, the invention concerns a device for treatments of endoscopic resection/removal of tissues comprising:

a handpiece apt to be held by an user;

an external tubular element comprising a proximal end, a distal end and a cutting aperture disposed at said distal end;

an internal tubular element apt to be pivotally received in said external tubular element and comprising a proximal end, a distal end and a cutting tip at its distal end;

guide means for rotating and/or oscillating said internal tubular element with respect to said external tubular element;

characterized in that:

said guide means comprise an electric motor and electric feeding means for the electric motor; and said guide means are contained inside said handpiece.

The device for treatments of endoscopic resection/removal of tissues according to the present invention is therefore free from a feeding wire as it has internally the guide means comprising motor and feeding means.

Therefore the ergonomics and the operative flexibility of the devices for treatments of endoscopic resection/removal are remarkably improved.

Nevertheless the personnel of the operation room must not perform anymore the maintenance of components such as the bracket and the pedal board if present, by making inspections which can require more complex technical interventions by qualified personnel.

The present invention, in the aforesaid aspect, can have at least one of the preferred characteristics which are described in the following.

According to a preferred aspect, the handpiece can comprise a control unit for regulating the guide means.

By providing the control unit inside said handpiece the maneuverability and the precision of the device are further improved.

Advantageously, the control unit can comprise at least an electronic circuit for regulating the functions and the speed of the electric motor and a plurality of pushbuttons.

Preferably, the device also comprises a transmission group of the motion actuated by the electric motor for rotating the internal tubular element with respect to the external tubular element.

Advantageously, the transmission group of the motion comprise at least a shaft pivotally supporting the internal tubular element and at least a control pinion which rotates the shaft, actuated by the electric motor.

Advantageously at least the aforesaid shaft can be made of plastic material, in this way further reducing the weight of the device in favour of the ergonomics and maneuverability of the device itself.

Preferably, the device can comprise a cooling circuit having a connection for a suction apparatus and a suction regulating device.

Advantageously the cooling circuit has a heat exchange portion with the electric motor for limiting the heating of the electric motor, in this way increasing the ergonomics of the device. Preferably the suction regulating device comprises a tap and a lever for controlling the tap from outside.

According to an advantageous aspect the electric motor is a brushless motor.

Preferably the handpiece is tight.

Advantageously, at least one between said handpiece and the guide means is disposable.

Preferably only the handpiece is disposable.

Further features and advantages of the invention will be more evident from the detailed description of some preferred but non exclusive embodiments of a device for treatments of endoscopic resection/removal of tissues, according to the present invention.

BRIEF DESCRIPTION OF THE DRAWINGS

Such description will be exposed here in the following with reference to the annexed drawings, given only for indication and therefore for a not limiting aim, in which.

DETAILED DESCRIPTION OF THE INVENTION

Figure 1:
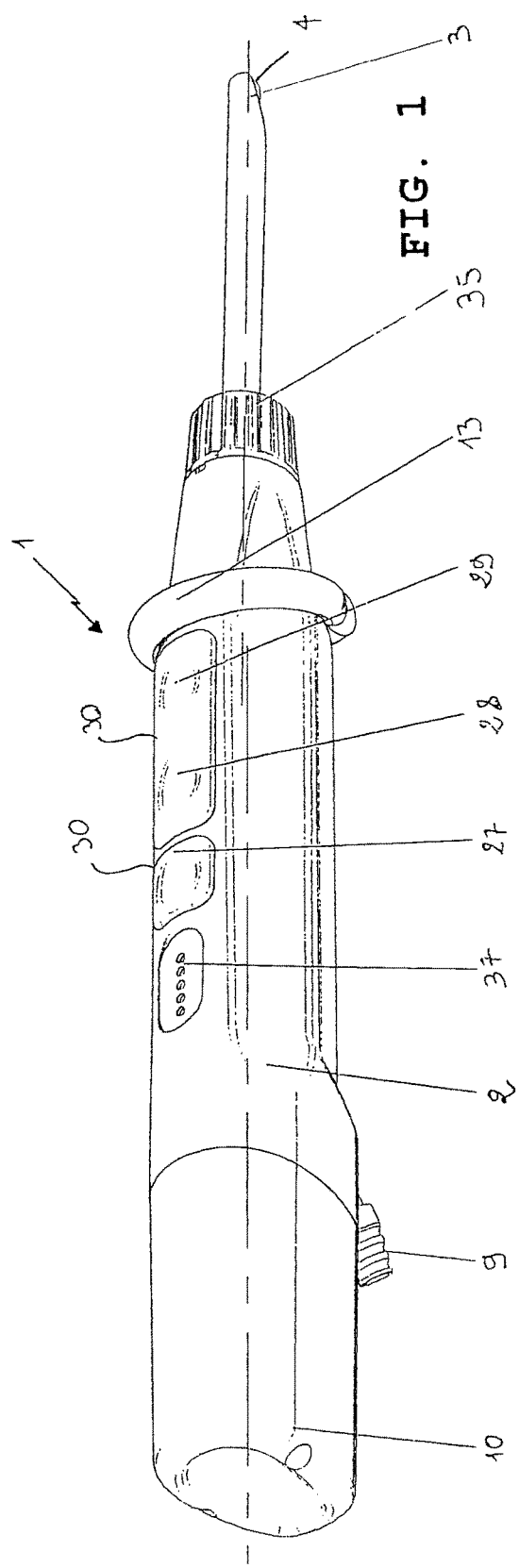
FIG. 1 is a side schematic view of a device for treatments of endoscopic resection/removal of tissues according to the present invention.
Figure 2:
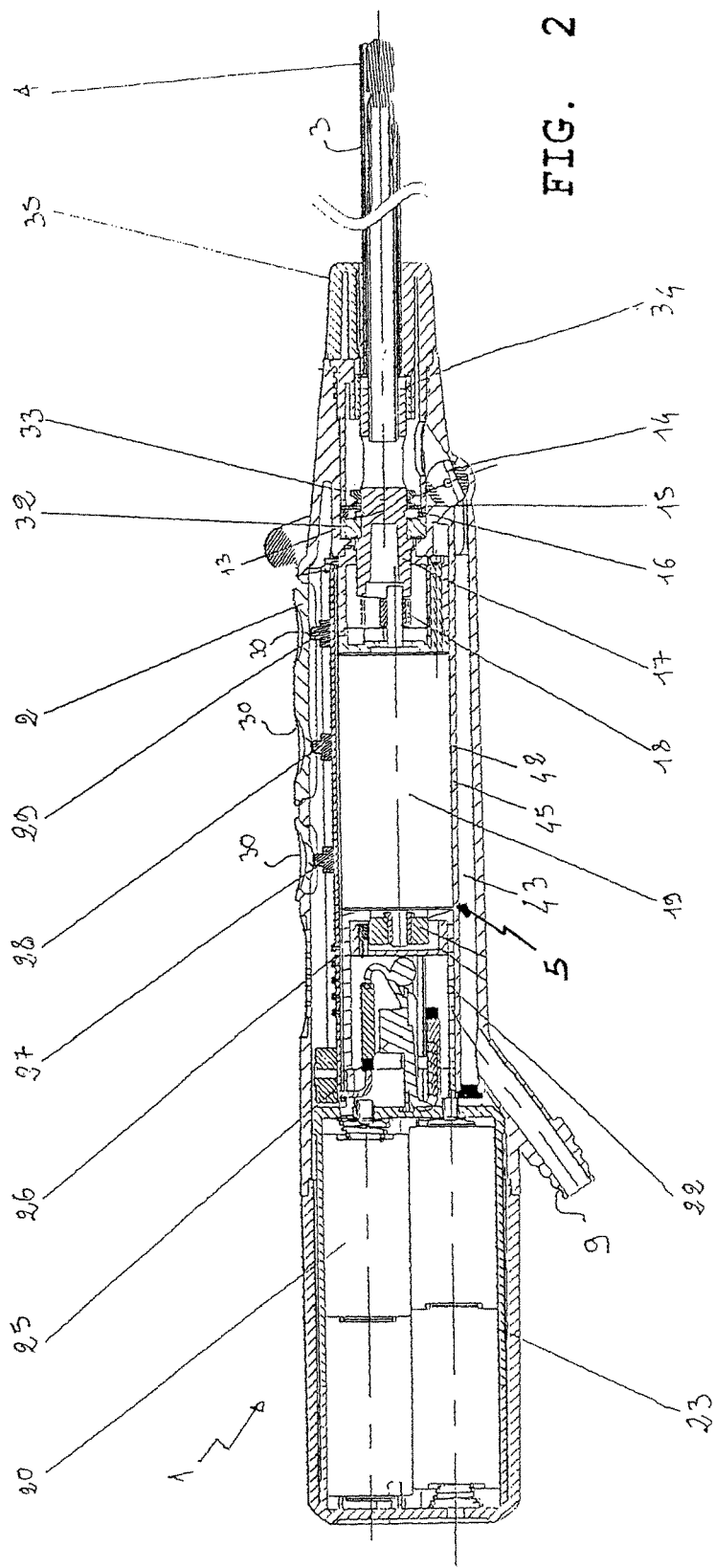
FIG. 2 is a side schematic view in section of a device for treatments of endoscopic resection/removal of tissues according to the present invention, angularly rotated with respect to FIG. 1.
Figure 3:
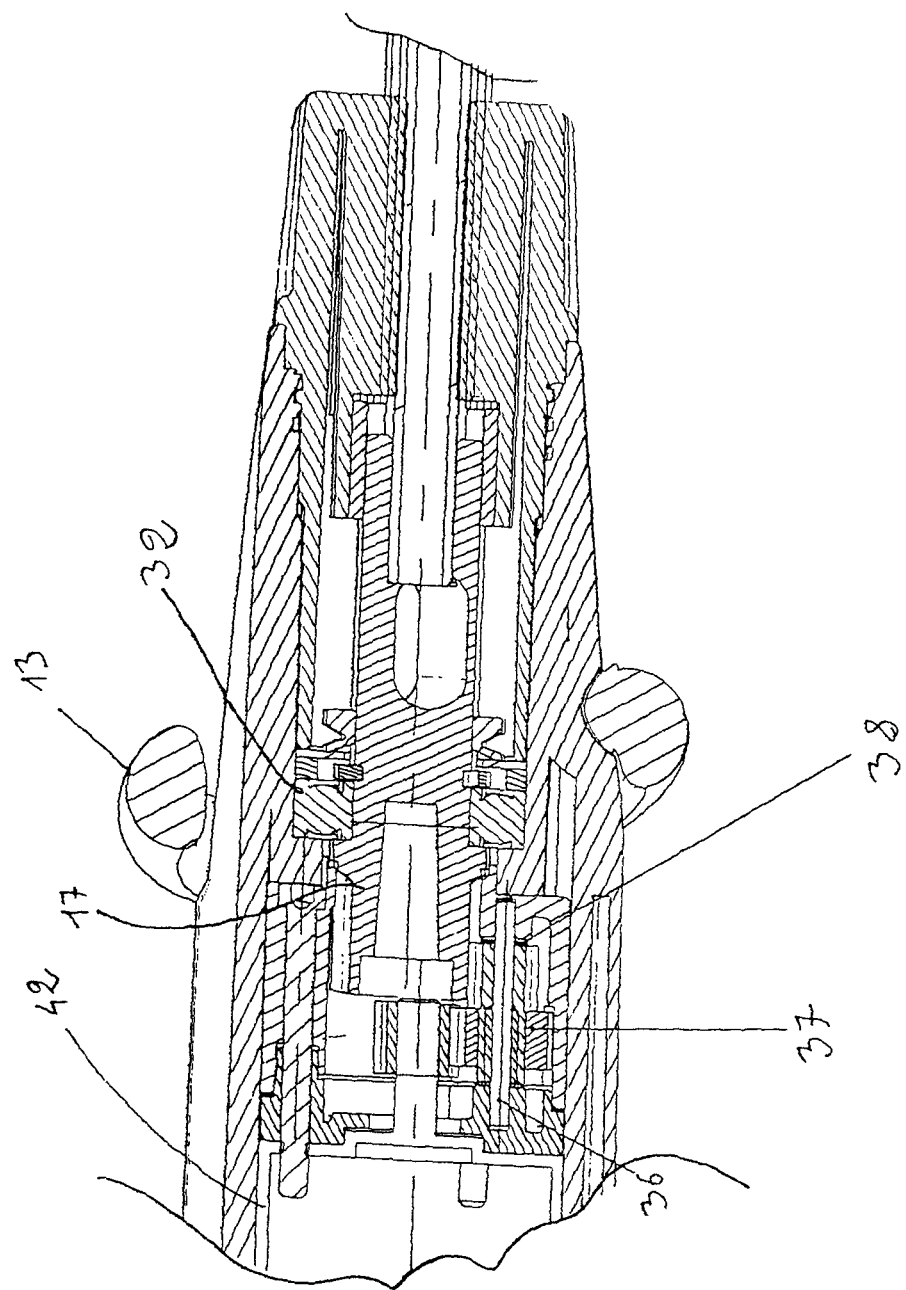
FIG. 3 is a sectional schematic view of an enlarged portion of the device in FIG. 2.

With reference to FIGS. 1-3, a device for treatments of endoscopic resection/removal of tissues is indicated with the reference character 1.

The device 1 for treatments of endoscopic resection/removal of tissues comprises a handpiece 2 apt to be held by an user, an external tubular element 3, an internal tubular element 4 and guide means 5 for rotating and/or oscillating the internal tubular element 4 with respect to the external tubular element 3.

The external tubular element 3 comprises a proximal end, a distal end and an aperture and/or cutting window disposed at the distal end.

The internal tubular element 4 is so shaped and dimensioned to be pivotally received into the external tubular element 3 and it comprises a proximal end, a distal end and a cutting tip at its distal end, facing the cutting window. The pivotal action of the internal tubular element 4 produces by abrasion the removal or the finishing of the tissue, and this process is defined as "resection".

The guide means 5 comprise an electric motor 19 and electric feeding means 20 for the electric motor 19. The electric feeding means 20 and the electric motor 19, according to a main aspect of the invention are fully received inside the handpiece 2.

The capacity of inserting into the handpiece all the functional parts of the device, in particular the electric motor 19 and the electric feeding means 20, permits to remarkably increase the maneuverability and the precision of motion of the device according to the present invention with respect to the cutting devices present in the market, made by arthroscopy.

The electric motor 19 is preferably a brushless type motor, but another type of electric motor with suitable dimensions and similar power could be apt to this aim. The motor 19 is able to rotate at a speed comprised between 400 and 4000 revolutions per minute.

The electric motor 19 is controlled by a unit that controls each function of the device 1, i.e. the starting, rotation or simple oscillation of the internal tubular element 4 with respect to the external tubular element 3 and the rotation speed of the internal tubular element 4.

The control unit comprises at least a main electronic circuit 26, supported by an electronic support circuit 22 and by an electronic auxiliary circuit 25.

The electronic support circuit 22 extends axially inside the handpiece 2 between the electric motor 19 and a container 23 of the electric feeding means 20, described below in more detail.

The main electronic circuit 26 is connected to pushbutton controls 27; 28, 29 which permit to select from outside the type of instruction to send to the main electronic circuit 26, i.e. the on or off-switching of the device 1, the type of oscillation/rotation of the internal tubular element 4 and the rotation speed.

Advantageously, a rubber protection 30 can be provided for the aforesaid pushbutton controls 27; 28, 29.

The device in FIG. 1 also shows five LEDs 37 connected to the control unit to indicate the set rotation speed.

Furthermore, it can be avoided that the personnel of the operation room making the treatment and management of the device must perform at the end of each operation the washing (with suitable disinfectants and detergents) and then the sterilizing of parts of the device.

The personnel of the operation room must not perform the storing of the device in suitable containers which can guarantee its sterility, with a consequent time and space consumption.

As can be seen in FIG. 1, the external tubular element is connected through a locknut 35 to the handpiece 2.

Inside the handpiece 2 a group of transmission of motion is present, comprising a reducer. In detail, the internal tubular element 4 is brought by a shaft 17 which through a motor pinion 18 functionally connects the internal tubular element with the electric motor 19.

Between the motor pinion 18 and the shaft 17 a rotary pin of the pinions is also provided with a first reduction 36, the pinions of the first reduction 37 and with trimming washers 38, as can be seen in FIG. 3.

The shaft 17 is supported in a pivotal way by a bearing 32 and by a bush 34, placed at the axially distal end with respect to the shaft 17.

Frontally, the group of transmission has a front gasket 33, tightly rotating with the shaft 17, also comprising two trimming washers 15 e 16. The front gasket 33 separates the group of transmission from a cooling circuit, as will be better described below.

The electric feeding means 20 are represented by alkaline batteries or lithium batteries, but any other kind of batteries could be used for this aim without departing from the scope of the present invention. The batteries are housed inside a container 23 provided at the proximal end of the handpiece 2.

The container 23 has electric connections suitable to feed the electric motor 19 and a non mobile cover 10 for changing the batteries and for inspection of the electric connections.

Preferably, the container 23 is also tight.

The electric motor 19 is housed in a motor frame 42 axially extending inside the handpiece 2.

The motor frame 42 centrally contains the motor pinion 18, in a proximal position at least part of the control unit controlling and regulating the motor 19 and frontally the group of transmission of motion.

Preferably, the device 1 according to the present invention comprises a suction and cooling circuit, having a connection 9 for a suction apparatus, outside the handpiece 2 and not shown in the figures, at least a duct 43 which guides from said connection 9 the cooling fluid to the internal tubular element 4 and to a suction regulating device.

The suction regulating device comprises a tap 14 and a lever 13 for controlling the tap 14 from outside. Advantageously the cooling circuit has a heat exchange portion 45 with said electric motor 19 for limiting its cooling.

To this aim, the heat exchange portion 45 axially extends inside the handpiece 1 in order to pass axially through the entire motor 19.

According to an advantageous aspect of the present invention the handpiece 2 is tight.

Figure 4:
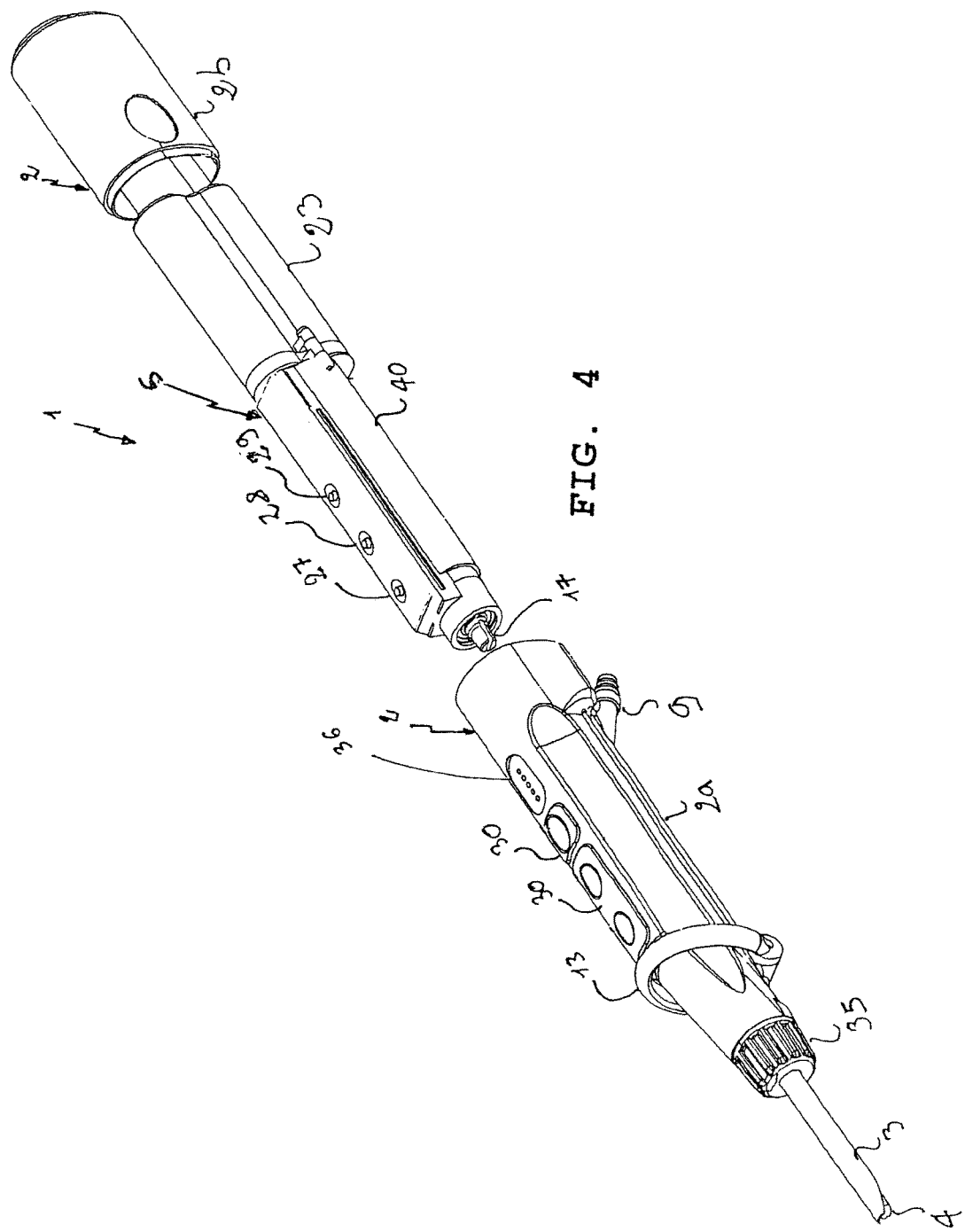
FIG. 4 is an exploded schematic view of an alternative embodiment of the device for treatments of endoscopic resection/removal of tissues, according to is the present invention.
Figure 5:
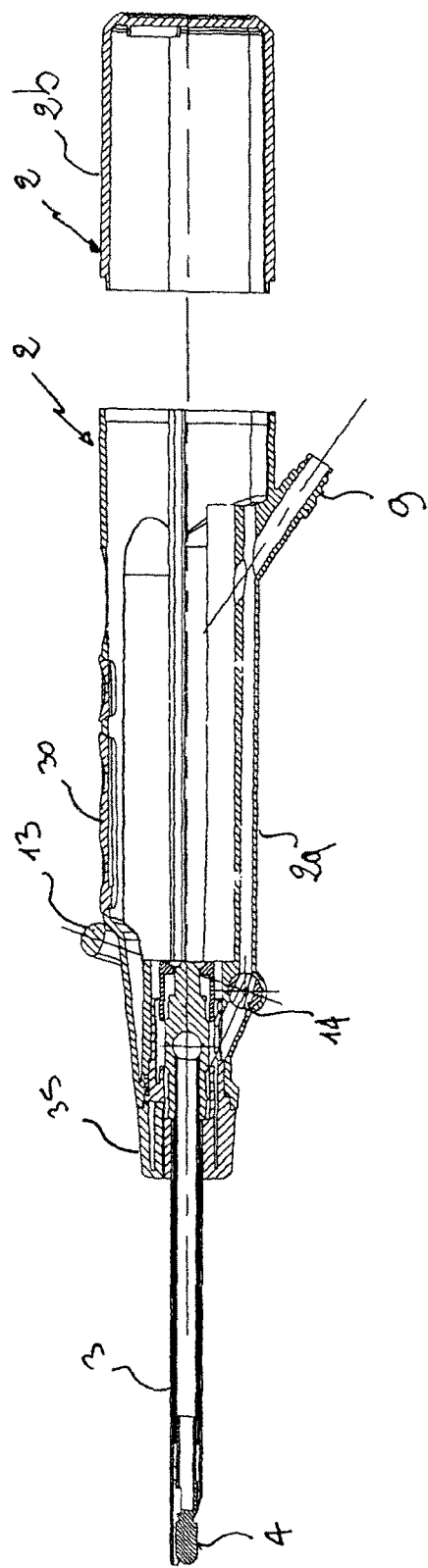
FIG. 5 is a side sectional schematic view of the handpiece of the device for treatments of endoscopic resection/removal of tissues shown in FIG. 4.
Figure 6:
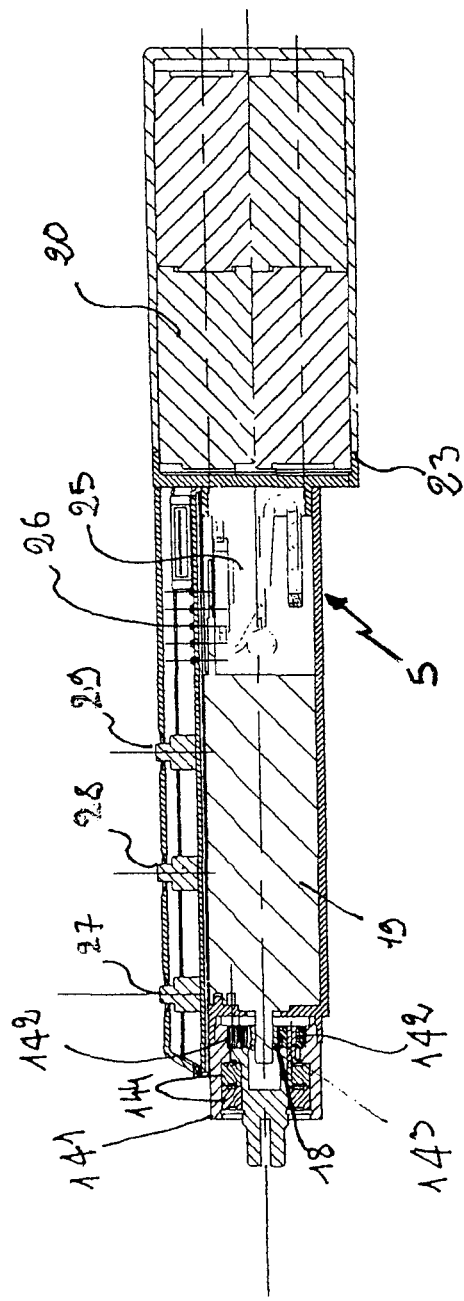
FIG. 6 is a sectional schematic view of an internal portion of the device in FIG. 4.

In the FIGS. 4-6 an alternative and preferred embodiment of the present invention is shown, completely similar to that of FIGS. 1-3, except the fact that at least a portion of the device 1, and in particular the handpiece 2 is disposable or single-used. To this aim, the guide means 5 are housed inside a suitable body 40 completely housed inside the handpiece 2.

In this way, the portion of the device which is more expensive, i.e. feeding means and motor, can be reused.

To permit a simple and rapid extraction of the guide means 5 with respect to the handpiece 2, said handpiece 2 can comprise a distal portion 2a supporting the external tubular element 3 and the internal tubular element 4 and a proximal end 2b engageable in a non mobile way with the distal portion 2a.

The ability to realize some parts, such as the handpiece 2, the external tubular element 3 and the internal disposable tubular element 4, i.e. single-used, reduces greatly in any case the problems relating to the storing and the sterilization of such parts by the personnel of the operation room.

Furthermore, the ability to insert inside the body 40 some functional parts of the device, in particular the electric motor 19 and the electric feeding means 20, permits to remarkably increase the maneuverability and the precision of motion of the device according to the present invention with respect to the cutting devices for arthroscopy, presently existing in the market.

In the embodiment shown in FIGS. 4-6 also the control unit is provided in the body 40.

The control unit comprises, also in this case, at least a main electronic circuit 26, supported by an electronic support circuit and by an auxiliary circuit 25.

The main electronic circuit 26 is connected to pushbutton controls 27; 28, 29 which permit to select from outside the type of instructions send to the main electronic circuit 26, i.e. the on or off-switching of the device 1, the type of oscillation/rotation function of the internal tubular element 4 and the pivotal speed.

Advantageously on the external handpiece for such aim a rubber protection 30 for the pushbuttons 27; 28, 29 can be provided, in a position corresponding to the aforesaid controls.

Preferably, according to this embodiment, inside the body 40 a group of transmission of motion is also present, comprising a reducer with satellites.

In detail, the internal tubular element 4 is brought by a shaft 17 which by a motor pinion 18 connects in a functional way the internal tubular element with the electric motor 19.

Between the motor pinion 18 and the shaft 17 a box 145 for the reducer with satellites 141 is also provided, comprising the satellites 142 and the support shaft 143 of the satellites.

The group 60 of the transmission of motion also has two radial bearings 144, radially juxtaposed between the motor shaft 17 and the box of the reducer with satellites.

The motor pinion 18 engages with the satellites 142 which transfer the motion to the shaft 17, through the support shaft 143 with satellites.

Alternatively to the just described coaxial transmission group a group of transmission of the chain could be provided, such as the one described in the embodiment of FIGS. 1-3 without departing from the protective scope of the present invention.

The electric feeding means 20 are represented by rechargeable alkalyne batteries or lithium batteries, but each other type of batteries could be used to this aim without departing from the protective scope of the present invention.

As shown in FIGS. 4 and 5, the batteries are housed inside a container 23 provided at the more proximal end of the body 40.

The container 23 has the electric connections suitable to feed the electric motor 19 and a non mobile cover to substitute the batteries and in order to permit inspections of the electric connections.

Preferably the container 23 is also tight.

In this embodiment, the electric motor 19 is housed inside the body 40 axially to the inside of the handpiece 2.

The body 40 centrally comprises the motor pinion 18, in a proximal position with respect to the control unit, which controls and regulates the motor 19 and frontally also the group of transmission of motion.

Preferably, even in this embodiment the device 1 comprises a suction and cooling circuit comprising a connection 9 for a suction apparatus, outside the handpiece 2 and not shown in the figures, at least a duct which from said connection 9 guides the cooling fluid to the internal tubular element 4 and a suction regulating device.

The suction regulating device also in this case comprises a tap 14 and a lever 13 to control the tap 14 from outside. Advantageously the cooling circuit has a heat exchange portion with said electric motor 19 to limit its heating.

The invention claimed is:

1. A device for endoscopic resection and removal of tissues, comprising:
   a handpiece configured to be held by a user;
      an external tubular element, comprising a proximal end, a distal end and a cutting aperture disposed at said distal end;
      an internal tubular element pivotally housed in said external tubular element and comprising a proximal end, a distal end and a cutting tip disposed at said distal end;
      a guide element, comprising an electric motor configured for rotating and/or oscillating said internal tubular element with respect to said external tubular element such that the cutting tip produces, by abrasion, removal and resection of the tissue, said motor operably linked to the proximal end of the internal tubular element, said guide element being a separate component contained inside said handpiece;
   a battery for the electric motor, said battery positioned proximal to said motor, and
   a suction and cooling circuit, the circuit comprising:
      a connection for a suction apparatus, the connection being positioned in a medial portion of the device, proximal to the electric motor and distal to the battery;
      a duct contained within the handpiece and extending from said connection, along and outside the motor from the proximal end of the motor to the distal end of the motor, and to the internal tubular element;
      a suction regulating device, comprising a tap and a pivotable lever provided on the handpiece for pivoting the tap; and
      a heat exchange portion of said electric motor, extending axially inside the handpiece, the heat exchange portion passing axially along the entire motor from the proximal end of the motor to the distal end of the motor;
   wherein the duct is configured to guide suction and a cooling fluid from the connection, through the heat exchange portion of the electric motor, and to the internal tubular element;
   wherein said handpiece comprises a control unit for regulating said guide element;
   and wherein the electric motor is controlled by the control unit which controls each function of the device, the control unit comprising at least a main electronic circuit, supported by an electronic support circuit and an electronic auxiliary circuit;
   the electronic support circuit physically extending axially inside the handpiece between the electric motor and a container of the battery;
   and wherein the main electronic circuit is connected to a plurality of individual pushbuttons located on the guide element inside the handpiece and alignable with associated button covers disposed on the handpiece and configured for selecting from outside the device, the type of instruction to send to the main electronic circuit.

2. The device according to claim 1, wherein said control unit regulates one or more functions of on or off-switching of the device, type of oscillation/rotation of the internal tubular element and rotation speed of said electric motor.

3. The device according to claim 1, wherein the device comprises a motion transmission element actuated by said electric motor and configured for rotating said internal tubular element with respect to said external tubular element.

4. The device according to claim 3, wherein said motion transmission element comprises:
   a shaft pivotally supporting said internal tubular element, and
   a control pinion for rotating said shaft, by actuation of said motor.

5. The device according to claim 4, further comprising a gasket tightly surrounding and rotatable with said shaft.

6. The device according to claim 1, wherein said electric motor is a brushless motor.

7. The device according to claim 1, wherein said guide element is housed inside a body that is insertable within and completely housed inside the handpiece.

8. The device according to claim 7, wherein only said handpiece is disposable.

9. The device according to claim 1, further comprising a rubber protection element configured to protect the push-button controls and disposed on the handpiece.

10. The device according to claim 1, wherein the pivotable lever arcuately surrounds the handpiece.

11. The device according to claim 1, wherein said duct is a common duct coupled to said suction apparatus and a cooling fluid source.

* * * * *